United States Patent [19]

Hedberg et al.

[11] Patent Number: 4,714,079
[45] Date of Patent: Dec. 22, 1987

[54] ATRIUM-CONTROLLED HEART PACEMAKER

[75] Inventors: Sven-Erik Hedberg, Kungsängen; Anders Lekholm, Bromma; Anders Lindgren, Täby, all of Sweden

[73] Assignee: Siemens Aktiengesellschaft, Berlin and Munich, Fed. Rep. of Germany

[21] Appl. No.: 910,998

[22] Filed: Sep. 24, 1986

[30] Foreign Application Priority Data

Oct. 4, 1985 [DE] Fed. Rep. of Germany ....... 3535568

[51] Int. Cl.$^4$ .............................................. A61N 1/36
[52] U.S. Cl. .............................................. 128/419 PG
[58] Field of Search ................................. 128/419 PG

[56] References Cited

U.S. PATENT DOCUMENTS

| 4,312,355 | 1/1982 | Funke | 128/419 PG |
| 4,363,325 | 12/1982 | Roline et al. | 128/419 PG |
| 4,541,430 | 9/1985 | Elmqvist et al. | |
| 4,554,921 | 11/1985 | Boute et al. | 128/419 PG |
| 4,574,437 | 3/1986 | Segerstad et al. | |
| 4,624,260 | 11/1986 | Baker, Jr. et al. | 128/419 PG |

FOREIGN PATENT DOCUMENTS 2142539 of 0000 United Kingdom .
2116845 of 0000 United Kingdom .
2076655 of 0000 United Kingdom .
2073023 of 0000 United Kingdom .

OTHER PUBLICATIONS

"Der Diagnostische Multiprogrammierbare Physiologische Impulsgenerator 674".

Primary Examiner—William E. Kamm
Assistant Examiner—Timothy Keegan
Attorney, Agent, or Firm—Hill, Van Santen, Steadman & Simpson

[57] ABSTRACT

An atrium-controlled heart pacemaker operates using set parameters including a smallest synchronous interval (SSI) between two stimulation pulses, a minimum atrial-ventricular delay time (AVmin) and a maximum atrial-ventricular delay time (AVmax). A control unit, dependent upon the appearance of an atrial signal, controls operation of the pacemaker such that the pacemaker operates with a variable pulse rate (DDD mode) when the atrial signal appears after a point in time SSI-AVmin, operates the pacemaker with a highest synchronous pulse rate when the atrial signal is between the points in time SSI-AVmin and SSI-AVmax, and causes no stimulation pulses to be emitted when the atrial signal appears before the point in time SSI-AVmax.

3 Claims, 2 Drawing Figures

ATRIUM-CONTROLLED HEART PACEMAKER

BACKGROUND OF THE INVENTION

The present invention relates to atrium-controlled pacemakers. In such pacemakers, stimulation of the heart occurs with a variable pulse repetition rate which depends upon the appearance of atrial signals. The pulse repetition rate may vary, for example, between 50 and 150 pulses per minute.

It is an object of the present invention to provide an atrium-controlled heart pacemaker such that physiologically unfavorable time intervals between atrial and ventricular activities are avoided in a Wenckebach mode wherein the spacing between two ventricular stimulation pulses or between a natural activity (QRS sequence) and a stimulation pulse is continuously varied.

The above object is achieved in accordance with the principles of the present invention by selecting a smallest synchronous interval (SSI) between two ventricular stimulation pulses or between a natural activity sequence and a stimulation pulse, as well as selecting a minimum and maximum atrial-ventricular delay time AVmin and AV max. A control unit is provided which, dependent upon the time of appearance of an atrial signal, controls operation of the heart pacemaker in one of several modes. If the atrial signal appears after a point in time SSI-AVmin, the heart pacemaker is operated with a variable pulse rate (DDD mode). When the atrial signal occurs between the point in time SSI-AVmin and the point in time SSI-AVmax, the control unit operates the heart pacemaker with a highest synchronous pulse rate. No stimulation pulses are produced when the atrial signal appears before the point in time SSI-AVmax.

In the pacemaker disclosed herein, a Wenckebach function is provided in that the AV delay is varied within a narrow, defined region, whereas the AV delay is lengthened only in the Wenckebach mode. The additional delay can become so large that the AV synchronism is lost during the Wenckebach mode. The Wenckebach function of the pacemaker is universal. If AVmin is established equal to the normal AV delay, the Wenckebach function of the pacemaker changes into a normal Wenckebach function in which a maximum delay is present.

DESCRIPTION OF THE DRAWINGS

FIG. 2 is a schematic circuit diagram for a heart pacemaker constructed in accordance with the principles of the present invention.

DESCRIPTION OF THE PREFERRED EMBODIMENTS

Figure 1:
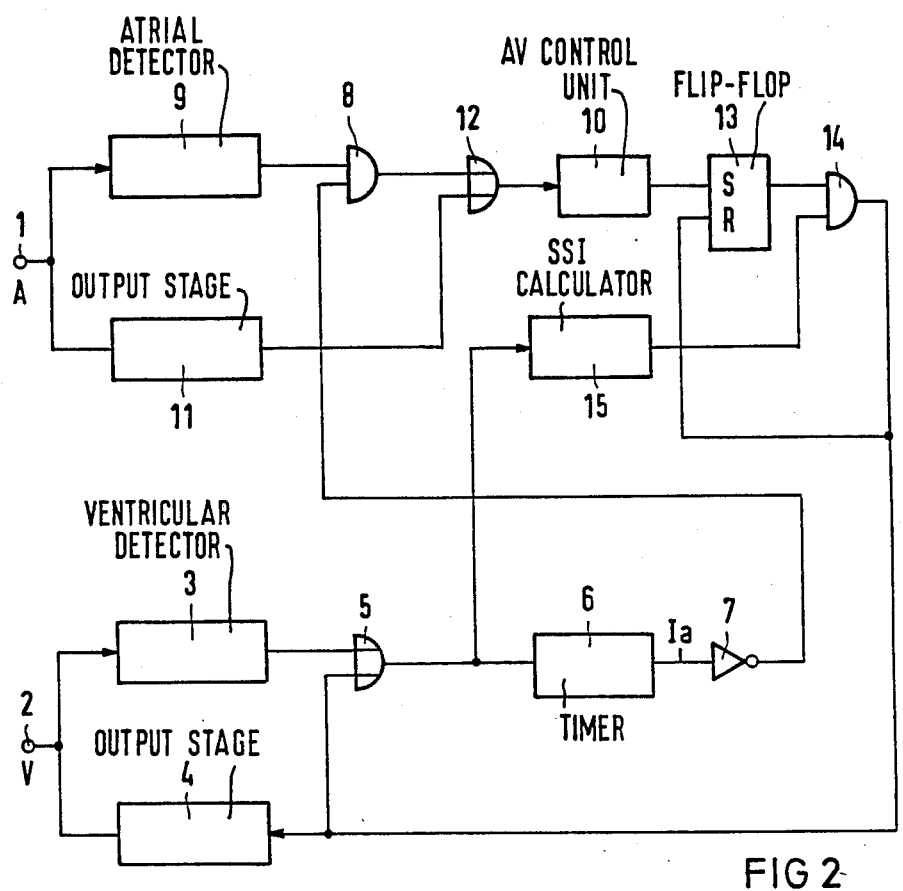
FIG. 1 is a graph showing the relationship of atrial signals to ventricular stimulation pulses in accordance with the principles of the present invention.
Figure 1:
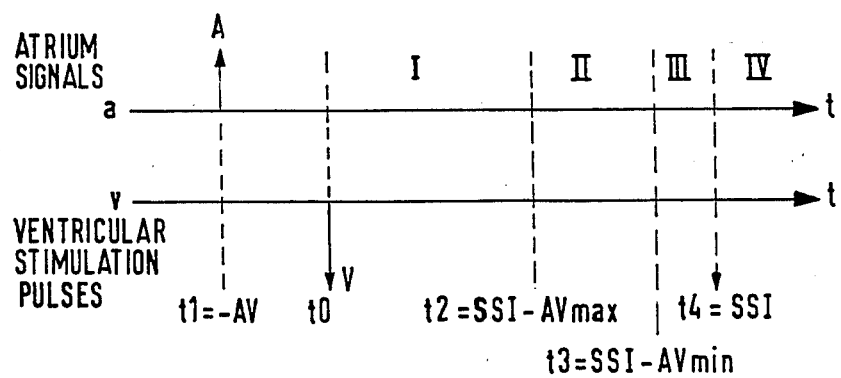

The various modes of operation of the heart pacemaker disclosed herein are shown in graph form in FIG. 1. The upper axis "a" shows the atrial signals with respect to time t, and the lower axis "v" shows the ventricular stimulation pulses with respect to time. An atrial signal A appears at a point in time $t1 = -AV$ when a stimulation pulse v appears at the point in time t0. The time between the atrial signal A and the stimulation pulse v, accordingly, is the AV delay. The heart pacemaker exhibits a minimum AV delay AVmin and a maximum AV delay AVmax. The pacemaker also exhibits a highest synchronous pulse rate which defines the smallest synchronous interval SSI between two ventricular stimulation pulses, or between a natural activity and a ventricular stimulation pulse. The smallest synchronous interval SSI is between t0 and t4. The point in time t3 represents a reduction of the interval SSI by the time AVmin. The point in time t2 represents a reduction of the interval SSI by the time AVmax. Accordingly, the time span shown in FIG. 1 can be subdivided into four intervals I, II, III and IV.

During normal operation with a variable pulse rate (DDD operation), the AV delay has a value between the points in time t0 and t1. When the pacemaker approaches the highest synchronous pulse rate, the AV delay remains constant until the interval between a ventricular and an atrial activity (VP interval) is equal to the difference between the smallest synchronous interval (SSI) and the smallest AV delay AVmin, this difference amounting to SSI-AVmin. For VP intervals in the region between the point time SSI-AVmax and SSI-AVmin, the ventricular stimulation interval (VV interval) remains constant and is equal to the smallest synchronous interval SSI. Under these conditions, the pacemaker exhibits the typical Wenckebach behavior of the variation of the AV delay given a constant VV interval.

No ventricular stimulation pulses are produced for those intervals between a ventricular stimulation pulse and the next P-wave which are less than SSI-AVmax.

Operation of the pacemaker disclosed herein can be summarized as follows:

| Appearance of an atrial Signal in: | Results In: |
|---|---|
| Region I | no ventricular stimulation |
| Region II | ventricular stimulation at t4 = SSI |
| Regions III, IV | normal DDD operation |

The exemplary embodiment shown in FIG. 2 has an atrial terminal 1 and a ventricular terminal 2. A ventricular detector 3 and an output stage 4, connected to the ventricular detector 2, emits a pulse at each ventricular detection and stimulation event, this pulse starting a timer 6 from an initial value via an OR gate 5. The output signal Ia of the timer 6 is a logic "1" when the timer 6 is within the region I of FIG. 1. The signal is inverted in a stage 7 and is supplied to an AND gate 8. The AND gate 8 prevents atrial detection pulses acquired by an atrial detector 9 from reaching the AV control unit 10 when the atrial signal occurs within the region I. Otherwise, each atrial signal signifies the start of an AV interval via an output stage 11 and an OR gate 12.

The output signal from the AV control unit 10 sets a flip-flop 13. The output signal from the flip-flop 13 is a logic "1" under such conditions, and is supplied to an AND gate 14 when the AV interval is at an end.

The output signal of the AND gate 14 resets the flip-flop 13 and generates a ventricular stimulation pulse via the output stage 4.

The same signal which starts the timer 6 also starts an SSI calculator 15. The output signal of the SSI calculator 15 is a logic "0" during the full SSI interval, and then changes to a logic "1". The standard Wenckebach function is obtained in this manner.

Although modifications and changes may be suggested by those skilled in the art it is the intention of the inventors to embody within the patent warranted hereon all changes and modifications as reasonably and properly come within the scope of their contribution to the art.

We claim as our invention:

1. An atrial-controlled heart pacemaker operable with a maximum AV delay (AVmax), a minimum AV delay (AVmin) and a smallest synchronous interval (SSI) between two ventricular stimulation pulses comprising:
   means for sensing an atrial event in said heart;
   means for sensing a ventricular event in said heart;
   means for supplying a ventricular pulse to said heart after an AV delay following a sensed atrial event;
   means for controlling said means for supplying said ventricular pulse for operating said pacemaker in a DDD mode when said sensed atrial event occurs after a point in time SSI-AVmin, operating said pacemaker at a highest synchronous rate corresponding to said SSI when said sensed atrial event occurs between points in time SSI-AVmin and SSI-AVmax, and causing no ventricular stimulation pulse to be supplied when said sensed atrial event occurs before said point in time SSI-AVmax;
   an AV control unit in said means for controlling, said AV control unit normally generating a signal upon the occurrence of each sensed atrial event for initiating generation of a ventricular pulse;
   means for inhibiting the transmission of said sensed atrial event to said AV-control unit when said sensed atrial event occurs before said point in time SSI-AVmax;
   a timer in said means for inhibiting, said timer having an input connected to said means for sensing said ventricular event, said timer assuming a first logic state at an output thereof for a period commencing with the occurrence with said ventricular event and concluding at said point in time SSI-AVmax, and thereafter assuming second logic state; and
   logic means in said means for inhibiting, said logic means having inputs connected to said means for sensing an atrial event and to said output of said timer, and having an output connected to an input of said AV control unit for preventing through-connection of said sensed atrial event to said input of said AV control unit while said output of said timer is in said first logic state.

2. An atrial-controlled heart pacemaker operable with a maximum AV delay (AVmax), a minimum AV delay (AVmin) and a smallest synchronous interval (SSI) between two ventricular stimulation pulses comprising;
   means for sensing an atrial event in said heart;
   means for sensing a ventricular event in said heart;
   means for supplying a ventricular pulse to said heart after an AV delay following a sensed atrial event;
   means for controlling said means for supplying said ventricular pulse for operating said pacemaker in a DDD mode when said sensed atrial event occurs after a point in time SSI-AVmin, operating said pacemaker at a highest synchronous rate corresponding to said SSI when said sensed atrial event occurs between points in time SSI-AVmin and SSI-AVmax, and causing no ventricular stimulation pulse to be supplied when said sensed atrial event occurs before said point in time SSI-AVmax;
   an AV control unit in said means for controlling, said AV control unit having an input connected to said means for sensing an atrial event for normally generating a pulse upon the occurrence of each sensed atrial event for initiating supply of a ventricular pulse to said heart;
   an SSI calculator in said means for controlling, said SSI calculator having an input connected to said means for sensing a ventricular event, said output of said SSI calculator assuming a first logic state for a period commencing with the occurrence of a ventricular event and concluding after said smallest synchronous interval, said output of said SSI calculator thereafter switching to a second logic state;
   a flip-flop having a set input connected to the output of said AV control unit for setting said flip-flop to said second logic state upon the occurrence of said output pulse from said AV control unit; and
   logic means having inputs respectively connected to the outputs of said flip-flop and said SSI calculator for generating said ventricular pulse at an output of said logic means when both outputs of said flip-flop and said SSI calculator assumes said second logic state.

3. An atrium control heart pacemaker as claimed in claim 2, wherein said flip-flop has a reset input connected to said output of said logic means for returning said output of said flip-flop to said first logic state upon the generation of said ventricular pulse.

* * * * *